United States Patent
Knudsen

(10) Patent No.: US 9,265,807 B1
(45) Date of Patent: Feb. 23, 2016

(54) MILKWEED SEED OIL ADMINISTERED TO ANIMALS

(71) Applicant: Natural Fibers Corporation, Ogallala, NE (US)

(72) Inventor: Herbert D. Knudsen, Ogallala, NE (US)

(73) Assignee: NATURAL FIBERS CORPORATION, Ogallala, NE (US)

( * ) Notice: Subject to any disclaimer, the term of this patent is extended or adjusted under 35 U.S.C. 154(b) by 345 days.

(21) Appl. No.: 13/910,499

(22) Filed: Jun. 5, 2013

Related U.S. Application Data

(60) Provisional application No. 61/655,645, filed on Jun. 5, 2012.

(51) Int. Cl.
| | | |
|---|---|---|
| *A61K 36/24* | (2006.01) | |
| *A61K 36/27* | (2006.01) | |
| *A61K 31/20* | (2006.01) | |
| *A61K 31/201* | (2006.01) | |
| *A61K 31/202* | (2006.01) | |

(52) U.S. Cl.
CPC .......... *A61K 36/27* (2013.01); *A61K 31/20* (2013.01); *A61K 31/201* (2013.01); *A61K 31/202* (2013.01)

(58) Field of Classification Search
CPC ...................................................... A61K 36/24
USPC ........................................................ 424/776
See application file for complete search history.

(56) References Cited

PUBLICATIONS

"Milkweed Oil: Packs a Punch to Pain:", the website: www.massageemag.com/miolkweed-oil-packs-a-punch-to-pain-9830/, by MASSAGE Magazine, Sep. 27, 2011.*

* cited by examiner

*Primary Examiner* — Chris R Tate
*Assistant Examiner* — Deborah Davis
(74) *Attorney, Agent, or Firm* — Curatolo Sidoti Co., LPA; Salvatore A. Sidoti; Daniel E. Moderick, Jr.

(57) ABSTRACT

Milkweed seed oil administered to an animal relieves the symptoms of fibromyalgia and improves the health of the animal. Administering an effective amount of milkweed seed oil orally or to the skin around or near the symptom of fibromyalgia of an animal results in relief from the symptoms of fibromyalgia as compared to the symptoms experienced by the animal both before the milkweed seed oil was administered.

27 Claims, No Drawings

MILKWEED SEED OIL ADMINISTERED TO ANIMALS

CROSS REFERENCE TO RELATED APPLICATIONS

This application claims the benefit of the filing date under 37 C.F.R. §119(e) from U.S. Provisional Application For Patent Ser. No. 61/655,645 filed Jun. 5, 2012, which is incorporated by reference in its entirety.

TECHNICAL FIELD

A composition and method are provided for improving mammalian animal health. Provided is a treatment method to improve the health of an animal suffering from fibromyalgia by treating an animal with milkweed seed oil in addition to or in substitution of other conventional treatment methods.

BACKGROUND

Fibromyalgia is a medical disorder characterized by chronic widespread pain and a heightened and painful response to pressure. The pain typically is associated with the muscoskeletal system and is typically present in one's joints, muscles, and tendons, in addition to other soft tissue. This disorder affects both men and women, with a ratio of nine women to one man. The symptoms of fibromyalgia can be extremely debilitating. In the United States, it is reported that over 12 million people suffer from fibromyalgia.

Fibromyalgia symptoms include not only pain and pressure sensitivity, but also debilitating fatigue, sleep disturbance and joint stiffness. Some people with fibromyalgia also report difficulty with swallowing, bowel movements, and bladder functions. Many people with fibromyalgia also exhibit conditions of depression and anxiety.

Current treatment of fibromyalgia includes medications, changes in behavior, and exercise. A host of medications are on the market which propose to deal with symptoms of fibromyalgia. Unfortunately, many of these medications offer very limited relief and some even have negative side effects. Quick, effective and positive treatments of fibromyalgia without negative side effects are desired in the art.

SUMMARY

Provided is a method for reducing the symptoms of fibromyalgia in an animal comprising administering an effective amount of a composition comprising milkweed seed oil to the animal.

Milkweed seed oil treatments of fibromyalgia have been shown to be effective in dealing with symptoms of fibromyalgia as discussed herein. Milkweed seed oil treatments have demonstrated positive results in connection with reducing or eliminating the symptoms of fibromyalgia without any of the negative side effects typically experienced with other medications. The improvement in animal health can be measured by monitoring the reduction in pain, pressure sensitivity, fatigue, and sleep disturbance in individuals diagnosed with fibromyalgia in addition to monitoring improvements in mood such as decreased levels of depression and anxiety.

DETAILED DESCRIPTION

Milkweed seed oil is administered to mammalian animals to reduce or alleviate the symptoms of fibromyalgia and to improve the animal health. In certain embodiments, the milkweed seed oil functions as an anti-inflammatory to fibromyalgia symptoms of inflamed nerves and/or over active nerves. The improvement in health is determined by the reduction in pain and the other symptoms of fibromyalgia and/or the reduced amount of other medications used to control pain and pressure sensitivity. Milkweed seed oil formulations may be administered to mammalian animals for non-therapeutic or therapeutic applications.

Milkweed seed oil as disclosed herein is a product comprised primarily of fatty acids and including small quantities of additional ingredients. The milkweed seed oil is administered topically, orally or internally to an animal in an amount and for a period of time sufficient to reduce or alleviate the symptoms of an animal having fibromyalgia.

Milkweed seed oil is produced from the seeds found in the pods of milkweed plants, which are known under the Latin binomial name *Asclepias*. Any of the numerous *Asclepias* plants can be used as a source of seed for producing milkweed seed oil. According to certain illustrative embodiments, the milkweed seed oil may be obtained from the milkweed seeds of *Asclepias Syriaca* and *Asclepias Speciosa*. Other non-limiting sources of milkweed seed oil may include, for example, *Asclepias albicans, Asclepias amplexicaulis, Asclepias californica, Asclepias cordifolia, Asclepias cryptocerus, Asclepias curassavica, Ascelpias eriocarpa, Ascelpias erosa, Ascelpias exaltat, Asclpeias fascicularis, Ascelpias fascicularis, Asclepias fruticosa, Asclepias humistrata, Asclepias incarnata, Ascelpias lanceolata, Ascelpias linaria, Asclepias linearis, Asclepias meadii, Ascelpias nyctaginifolia, Ascelpias obovata, Ascelpias physiocarpa, Asclepias purpurascens, Asclepias quadrifolia, Asclepias solanoana, Asclepias speciosa, Asclepias subulata, Asclepias sullivantii, Asclepias syriaca, Asclepias tuberose, Asclepias variegate, Asclepias verticallata, Asclepias vestita* and *Asclepias vincetoxicum*. This list of *Asclepias* species is not exhaustive as scientists believe that there may be over 800 different varieties of *Asclepias*.

Production of Milkweed Seed Oil.

In certain embodiments, milkweed seed oil is produced by cold pressing substantially clean milkweed seeds in a seed press or by extracting the oil from the seed with a non-polar solvent to recover the milkweed seed oil. Suitable non-polar solvents include but are not limited to hexane, carbon dioxide and petroleum ether. Extraction with these solvents produces a liquid lipid product comprising primarily fatty acids, and in certain embodiments, a liquid lipid product of fatty acids.

Milkweed seed may also contain toxic cardenolides that can be recovered from the milkweed seed with a polar solvent as a powder or as a dissolved solid in the polar solvent. Non-polar solvents used in extracting the fatty acids from the seed may be selected so that the effectiveness of the milkweed seed oil is not impaired by the presence of cardenolides. Rogers E. Harry-Okuru and Thomas P. Abbott in Industrial Crops and Products 7 (1997) 53-58 concluded that "Cold-pressed and solvent (petroleum ether) extracted milkweed oils show no detectable cardenolides by the alkaline TNBP method at a limit of less than 1.0 ppm." In one embodiment, milkweed seed oil is produced that has no detectable cardenolides at a limit of less than 1 part per million.

Raw milkweed seed oil produced in pressing equipment or in extraction with a solvent may need to be filtered to remove fine particles of the milkweed seed. This can be accomplished with traditional seed oil separating equipment, efficient filtration systems or with other known means of separation.

A typical fatty acid profile of milkweed seed oil produced in a seed press is shown below in Table I. As can be deduced from the data, the milkweed seed oil had a large majority of fatty acids commonly found in food grade vegetable oils. The oil also contained two less common fatty acids, C16:1 palmitoleic acid and C18:1 cis-vaccenic acid. The milkweed seed oil with the fatty acid profile in Table I was used in the experiments described below.

TABLE I

Milkweed Seed Oil Fatty Acid Profile

| >1% Concentration | |
|---|---|
| C16:0 Palmitic Acid | ~6.6% |
| C16:1 n-7 Palmitoleic Acid | ~11.8% |
| C17:0 Heptadecanoic Acid | ~2.4% |
| C18:1 n-9 Oleic Acid | ~23.9% |
| C18:1 n-7 cis-Vaccenic acid | ~12.4% |
| C18:2 Linoleic Acid | ~40.4% |
| C18:3 Linolenic Acid | ~1.3% |

In addition to the fatty acids shown in the table above, a minor amount of other fatty acids which are present at concentrations below 1% of the oil were in the milkweed seed oil recovered. Those fatty acids include the following:

TABLE II

Milkweed Seed Oil Fatty Acid Profile

| <1% Concentration | |
|---|---|
| C17:1 10-Heptadecanoic Acid | ~0.2 |
| C18:0 Stearic Acid | ~0.2 |
| C20:0 Arachidic Acid | ~0.5 |
| C20:1 Eicosenoic Acid | ~0.2 |
| C22:2 Docosadienoic Acid | ~0.4 |
| C23:0 Tricosanoic Acid | ~0.4 |
| C24:0 Lignoceric Acid | ~0.4 |
| C24:1 Nervonic Acid | ~0.2 |

Milkweed seed oil may also contain other components in lesser amounts. Other ingredients identified in the oil used in the experiment below include phospholipids (about 2.15 g/100 g), digitoxin like components (about 890 mg/100 g), stigmasterol (about 272.8 mg/100 g), alpha-tocopherol (about 37.8 mg/100 g), β-sitosterol (about 23.7 mg/100 g), and campesterol (about 13.6 mg/100 g). In addition, vitamins, phytosterols, carotenes and other trace ingredients found in milkweed seed oil may have a positive impact on animal health even at very low concentrations.

Milkweed seed used to produce milkweed seed oil differs based on the genetic line of *Asclepias* used in production, the weather during the milkweed pod growth and the geographical region where the milkweed was grown. These variations, however, produce seed with oil contents within the limits of the current composition and method.

Also, milkweed seed oil may be produced not only from milkweed seed, but also from milkweed seed oil press cake. Press cake is the solid discharge from a seed press after some but not all of the oil is pressed out of the seed. The milkweed seed oil press cake can be rerun in a press to produce more milkweed seed oil or the press cake can be solvent extracted. Press cake extractions may provide unique, but similar fatty acid profiles to the data shown in Table I. Milkweed seed oil from these sources are effective according to the present composition and method, provided that liquid fatty acid oil is recovered and that cardenolides are not present in the oil at a level that is harmful to the animal. In most embodiments such cardenolides are below about 1 part per million.

Factors Affecting the Application of Milkweed Seed Oil to Animals.

A method is provided for improving the health of a mammalian animal and for reducing or alleviating the symptoms of fibromyalgia. The method comprises administering an effective amount of the disclosed milkweed seed oil formulation to an animal. Milkweed seed oil may be administered to animals topically, orally or internally. In certain embodiments, the amount administered daily measured as 100% milkweed seed oil is less than about 5 grams per kilogram of body weight, and in some embodiments is less than about 1 gram per kilogram of body weight. Lower amounts of milkweed seed oil, such as about 0.1 gram per kilogram of body weight per day and even about 0.01 gram per kilogram of body weight per day have been proven effective.

For topical applications, milkweed seed oil can be administered to any area of the skin over areas experiencing the symptoms of fibromyalgia. Milkweed seed oil can be applied to the upper body, such as the head, neck and shoulders. The oil can also be administered to the arms in places like the elbows, wrist and hands. Also in other uses, the milkweed seed oil can be administered to the hips, the legs and the feet of the animal.

The milkweed seed oil penetrates through the skin quickly. The milkweed seed formulation may be incorporated into a wide variety product forms for topical administration to a subject. The milkweed seed formulation may be incorporated into a product for topical administration to a subject by combining the milkweed seed formulation with a topical product base. By way of illustration, but not of limitation, the milkweed seed oil may be incorporated into topical balms, creams, gels, lotions, ointments, salves, sprays (aerosol and non-aerosol sprays), rollerballs and dermal patches for topical administration of the milkweed seed oil formulation.

The milkweed seed oil liquid formulation administered to an animal may be milkweed seed oil alone or milkweed seed oil in combination with other ingredients that do not block the beneficial effect of milkweed seed oil. Formulated compositions of liquid milkweed seed oil and other components are included as embodiments of the present composition and method. The concentration of milkweed seed oil in certain embodiments is about 50 weight % or more of the compositional formulation. In other embodiments, the concentration of milkweed seed oil is about 60 weight % or more of the compositional formulation. In still other embodiments, the concentration of milkweed seed oil is about 40 weight % or more of the compositional formulation.

Optional compatible ingredients in milkweed seed oil liquid formulations include at least one of food grade vegetable oils, nut oils, fish oils, fragrances and other seed oils. Jojoba oil may also be used effectively in combination with milkweed seed oil. Suitable vegetable oils include but are not limited to at least one of olive oil, canola oil, safflower oil, corn oil, soybean oil, sunflower seed oil, or flax oil. Suitable nut oils include but are not limited to at least one of walnut oil, almond oil, or macadamia nut oil. A wide range of fragrances are available commercially that may be included in the milkweed seed oil formulation to alter the odor of the milkweed seed oil product formulation.

The dosage of the milkweed seed oil administered to an animal depends on the concentration of the milkweed seed oil in the formulation. In topical applications, excellent results have been obtained on about a 55 kilogram animal using a formulation comprising about 100% milkweed seed oil in a dose of about 0.3 gram per application, 2 times per day, in separated periods of time. An acceptable administration rate to the animal is a daily amount of about 0.006 grams per kilogram of body weight. This dosage is within an acceptable daily rate of administration—less than about 0.01 grams per kilogram of body weight. The same amount of milkweed seed oil could be administered using about one gram doses of a blend containing from about 20% to about 30% milkweed seed oil and from about 70% to about 80% vegetable or jojoba oil.

Evidence indicates that total daily use of less than about 20 grams of milkweed seed oil, calculated as 100% milkweed seed oil, is more than sufficient to produce the desired improvement in reducing fibromyalgia pain. The dosage of milkweed seed oil taken orally or internally rather than topically may vary from these general guidelines for topical applications. Experience has shown that the animal administered milkweed seed oil topically demonstrates the impact of the formulation on the body of the animal. Changes in the dosage may be necessary in response to these observations.

Suitable ranges of milkweed seed oil dosages are shown by the non-limiting experimental tests below. Higher dosages or longer usage of milkweed seed oil could further improve health managing pain. It may be necessary to continue milkweed seed oil treatment to maintain the improved relief results, but there is evidence that milkweed seed oil has a positive impact on fibromyalgia for a few days after daily application or consumption terminates. The need to have an effective amount of milkweed seed oil may require the user to alter the dosage over time to provide the desired benefits as measured by the difference in the level of pain.

Oral administration of milkweed seed oil has also been found to be beneficial in relieving symptoms of fibromyalgia pain.

Milkweed seed oil may be formulated into a wide variety of orally ingestible compositions. Liquid forms include solutions, suspensions, emulsions, gels, syrups, liquid-containing capsules, and the like. According to certain embodiments, the liquid milkweed seed oil formulation is contained within an orally ingestible capsule. Upon ingestion, the liquid-containing capsule is digested and the liquid milkweed seed oil formulation is released from the capsule.

According to certain illustrative embodiments, the milkweed seed oil may be formulated with an orally ingestible carrier such as an orally ingestible liquid carrier to provide an orally ingestible milkweed seed oil. For example, the milkweed seed oil may be formulated with an orally ingestible liquid carrier to provide a beverage or liquid nutritional supplement. The beverages may be provided ready for oral ingestion or may be provided in a concentrate that requires dilution with acceptable liquids prior to oral ingestion. According to other embodiments, the milkweed seed oil may be formulated into other solid orally ingestible product forms or carriers, such as powders, pills, lozenges, tablets, caplets, capsules, gel capsules, edible films, and the like. Flavoring agents may also be added to the orally ingestible products to provide a more palatable orally ingestible composition.

The orally ingestible milkweed seed oil formulation may further include nutritionally effective amounts of an additional agent. According to certain embodiments, the milkweed seed oil formulation may further comprise effective amounts of at least one vitamin, or at least one mineral or a combination of at least one vitamin and at least one mineral. According to certain embodiments, the milkweed seed oil formulation comprises a nutritionally effective amount of milkweed seed oil and a nutritionally effective amount of at least one vitamin. According to certain embodiments, the milkweed seed oil formulation may comprise a nutritionally effective amount of milkweed seed oil and a nutritionally effective amount of at least one vitamin. According to certain embodiments, the milkweed seed oil may comprise a nutritionally effective amount of milkweed seed oil formulation and a nutritionally effective amount of at least one vitamin and at least one mineral. The milkweed seed oil formulation may also include at least one amino acid alone or at least one amino acid in combination with at least one vitamin and/or at least one mineral.

Experimental Production of Milkweed Seed Oil in a Seed Press.

According to these experiments, clean milkweed seed from *Asclepias Syriaca* and *Asclepias Speciosa* plants was pressed in a screw press to produce raw milkweed seed oil. The raw oil was strained in two layers of high thread count cotton fabric at atmospheric pressure to produce clean milkweed seed oil. The clean milkweed seed oil was placed in a marked container, sealed and placed in a constant temperature room maintained at about 70 degrees Fahrenheit. Samples of milkweed seed oil for the experiments described below were taken from the stored oil and maintained in marked sealed bottles. The fatty acid profile of milkweed seed oil produced in this experiment is shown above in Table I and Table II.

Experimental Testing of Milkweed Seed Oil Properties.

The milkweed seed oil produced above was tested by a certified, independent laboratory that specializes in natural oil analysis. A sample of milkweed seed oil from this production run was analyzed for antioxidant capacity. Oxygen Radical Absorbance Capacity (ORAC) tests conducted on milkweed seed oil tested for total antioxidant capacity showed results of 9,700 micromoles of Trolox equivalents per 100 grams. This rating is about 50% higher than the published rating of blueberries.

Experimental Testing of Milkweed Seed Oil Administered to a 49 Year Old Female Suffering from Fibromyalgia.

A test to determine the impact of milkweed seed oil treatment was conducted on a 49 year old female human who has fibromyalgia. She began to notice symptoms of fibromyalgia in junior high school. The symptoms of fibromyalgia increased with age and for over 17 years fibromyalgia has chronically been a major problem for her. The milkweed seed oil used in this experimental testing comprised liquid fatty acid oil of 98.5% milkweed seed oil, 1% crude soy bean oil and 0.5% unrefined jojoba oil. The woman applied the milkweed seed oil blend on to her skin topically with a roller ball bottle holding 9.6 ml of oil. She rolled on the oil blend in any area of pain all over her body as she discovered it. The main areas treated were her neck, shoulders, hips, arms, elbows and wrist. This application of milkweed seed oil blend was conducted one or two times a day for as long as she felt she needed the application. The woman continued her use of milkweed seed oil daily for 2 months. At the end of the two month test, 1 ml of the oil blend remained in the bottle, which calculates into use of 8.6 ml over the two month test.

At the beginning of the test, the woman was asked to quantify her level of pain and mobility on a scale of 1 to 5. In this scale, the rating of 5 was major pain problems and/or major mobility problems. At the beginning of the test, the woman measured her pain problem at 5, major pain problems. She also measured her mobility problem at 5, major mobility problems. At the end of the two month test, the woman rated her pain problem at 1-2. A rating of 1 means no pain is present and a rating of 2 means a little pain is present. At the end of the two month test, the woman also rated her mobility problem as a 2 on the scale of 1 to 5. A rating of 2 means little mobility problems are present. At the end of the test, the woman stated that she had previously tried to control her fibromyalgia with many different medications, treatments and supplements. The test subject stated that the milkweed seed oil blend was the first thing topically that has ever worked. The woman also stated that she observed no negative side effects with her milkweed seed oil treatment.

From the test results with this woman, it was concluded that the milkweed seed oil applied topically to the areas of pain and immobility from fibromyalgia was positively affected by the treatment. The woman also said that she was delighted by the results she experienced with the use of the milkweed seed oil blend.

There are many possible treatments of animals with milkweed seed oil to alleviate symptoms of fibromyalgia according to the compositions and methods discussed and exemplified herein. Although the embodiments have been described in detail through the above description and the preceding examples, these examples are for the purpose of illustration only and it is understood that variations and modifications can be made by one skilled in the art to identify and administer these treatments using milkweed seed oil without departing from the spirit and the scope of the disclosure. It should be understood that the embodiments described above are not only in the alternative, but can be combined.

What is claimed is:

1. A method for reducing the symptoms of fibromyalgia in an animal suffering therefrom comprising administering to the animal an effective amount of a composition comprising milkweed seed oil obtained from an *Asclepias* plant.

2. The method of claim 1, wherein the animal is a human being.

3. The method of claim 1, wherein the symptoms of fibromyalgia are inflamed nerves or over active nerves.

4. The method of claim 1, wherein the animal is a human being suffering from fibromyalgia in the upper body.

5. The method of claim 1, wherein the animal is a human being suffering from fibromyalgia in the arms.

6. The method of claim 1, wherein the animal is a human being suffering from fibromyalgia in the hips.

7. The method of claim 1, wherein the animal is a human being suffering from fibromyalgia in the legs.

8. The method of claim 1, wherein the animal is a human being suffering from fibromyalgia in the feet.

9. The method of claim 1, wherein the source of the milkweed seeds used for producing the milkweed seed oil comes from any one of the following plants: *Asclepias syriaca, Asclepias speciosa, Asclepias albicans, Asclepias amplexicaulis, Asclepias californica, Asclepias cordifolia, Asclepias cryptocerus, Asclepias curassavica, Asclepias eriocarpa, Asclepias erosa, Ascelpias exaltat, Asclpeias fascicularis, Ascelpias fascicularis, Asclepias fruticosa, Asclepias humistrata, Asclepias incarnata, Asclepias lanceolata, Ascelpias linaria, Asclepias linearis, Asclepias meadii, Asclepias nyctaginifolia, Ascelpias obovata, Ascelpias physiocarpa, Asclepias purpurascens, Asclepias quadrifolia, Asclepias solanoana, Asclepias speciosa, Asclepias subulata, Asclepias sullivantii, Asclepias syriaca, Asclepias tuberose, Asclepias variegate, Asclepias verticallata, Asclepias vestita, Asclepias vincetoxicum*, or mixtures thereof.

10. The method of claim 1, wherein the composition comprises at least one of amino acids, food grade vegetable oils, nut oils, fragrances, vitamins, minerals, flavoring agents, other seed oils, or mixtures thereof.

11. The method of claim 10, wherein the food grade vegetable oils comprise at least one of olive oil, canola oil, safflower oil, corn oil, soybean oil, sunflower seed oil, flax oil, or mixtures thereof.

12. The method of claim 10, wherein the nut oils comprise at least one of walnut oil, almond oil, macadamia nut oil, or mixtures thereof.

13. The method of claim 1, wherein the composition further comprises jojoba oil.

14. The method of claim 1, wherein the composition further comprises jojoba oil and soybean oil.

15. The method of claim 1, wherein the composition is formulated into an orally ingestible product or a topically administered product.

16. The method of claim 15, wherein the composition comprises an orally ingestible product comprising a therapeutically effective amount of milkweed seed oil.

17. The method of claim 16, wherein the orally ingestible product is in a liquid form or a solid form.

18. The method of claim 17, wherein the liquid form is selected from the group consisting of solutions, suspensions, emulsions, gels, syrups, liquid-containing capsules, and mixtures thereof.

19. The method of claim 17, wherein the solid form is selected from the group consisting from powders, pills, lozenges, tablets, caplets, capsules, gel capsules, edible films, and mixtures thereof.

20. The method of claim 1, wherein the composition comprises a topically administered product comprising a therapeutically effective amount of milkweed seed oil.

21. The method of claim 20, wherein topically administered product comprises topical balms, creams, gels, lotions, ointments, salves, sprays, rollerballs and dermal patches.

22. The method of claim 21, wherein the spray comprises an aerosol spray or a non-aerosol spray.

23. The method of claim 1, wherein the amount of milkweed seed oil administered to the animal per day is less than about 5 grams per kilogram of body weight.

24. The method of claim 1, wherein the amount of milkweed seed oil administered to the animal per day is less than about 0.1 grams per kilogram of body weight.

25. The method of claim 1, wherein the amount of milkweed seed oil administered to the animal per day is less than about 0.01 grams per kilogram of body weight.

26. The method of claim 1, wherein the symptom of fibromyalgia is pain.

27. The method of claim 1, wherein the symptom of fibromyalgia is pressure sensitivity.

\* \* \* \* \*